United States Patent [19]

Miodownik

[11] 4,325,382
[45] Apr. 20, 1982

[54] PROCESS AND APPARATUS FOR THE REAL TIME ADAPTIVE FILTERING OF CATHETER PRESSURE MEASUREMENTS

[75] Inventor: Saul Miodownik, New York, N.Y.

[73] Assignee: Memorial Hospital for Cancer and Allied Diseases, New York, N.Y.

[21] Appl. No.: 150,014

[22] Filed: May 15, 1980

[51] Int. Cl.$^3$ ............................................... A61B 5/02
[52] U.S. Cl. .................................... 128/673; 73/4 R; 367/43-46
[58] Field of Search .............................. 128/672-675, 128/687-690; 364/415, 572, 724, 825; 333/175-176; 307/167; 73/4 R

[56] References Cited

U.S. PATENT DOCUMENTS 4,232,373 11/1980 Jackson et al. ................. 364/724 X

OTHER PUBLICATIONS

Brower, R. W. et al., "A Fully Automotic Device for Compensating for Artifacts in Conventional Catheter-Monometer Pressure Recordings", BME (GB) V10#8 Aug. 1972. pp. 305-310.

Parson, I.D. et al., "Negative Feedback Applied to Pressure Transducers" MBE vol. 14 #6 pp. 591-598 Nov. 1976.

Damenstein, A. et al., "Electronic Compensator for Pressure Waveform Distortion by Fluid-filled Catheters", MBE vol. 14#2 pp. 186-192 Mar. 1976.

*Primary Examiner*—Robert W. Michell
*Assistant Examiner*—Francis J. Jaworski
*Attorney, Agent, or Firm*—Felfe & Lynch

[57] ABSTRACT

A process and apparatus for measuring the catheter fluid pressure of a patient wherein a pressure transducer is used to convert the pressure into an electrical signal and a pressure indicator indicates the pressure corresponding to the electrical signal. A turnable active filter is disposed in the signal path between the transducer and the pressure indicator and the frequency parameters of the filter are adapted to that of the catheter in real time.

18 Claims, 6 Drawing Figures

PROCESS AND APPARATUS FOR THE REAL TIME ADAPTIVE FILTERING OF CATHETER PRESSURE MEASUREMENTS

BACKGROUND OF THE INVENTION

The present invention relates to an apparatus and process for the electrical filtering of pressure measurements of the fluid pressure in a catheter.

The proliferation of intra-arterial pressure measurements and the associated technology has implied a greater degree of accuracy and confidence in the measurements than can often be realized. Among the multitude of considerations that are related to a catheter-manometer system, is that of frequency response. The addition of a rigid, fluid filled pressure transmission line, connecting the patient's arterial cannula or catheter to a pressure transducer will generally reduce the overall system frequency response. The formation of bubbles in the hydraulic system may introduce resonances at frequencies that will severely compromise the quality of the pressure waveform and the systolic values derived from it.

Despite careful attention by nursing and medical staff including frequent flushing, tightening of stopcocks and hardware, etc., inaccuracies introduced by the pressure system resonance are all too often present and remain to be dealt with.

In prior art apparatus, attempts have been made to address this problem with low pass filters that roll off the frequency response of the pressure amplifier at some frequency considered to be the lower limit of the unwanted resonance. Unfortunately, much theoretical and empirical evidence indicates that these resonances are very close to the primary frequency components of the waveform itself. In addition, as the hydraulic system ages, minute bubbles form that tend to shift the resonance to increasingly lower frequencies.

SUMMARY OF THE INVENTION

The main object of the present invention is to provide a process and an apparatus for compensating for the wide variations of resonance frequency, various transmission line lengths and system aging.

This and other objects of the present invention are achieved by the real time adaptive filtering of the output of a pressure transducer in order to adapt the filter to the particular frequency characteristics of the system.

This is carried out by interrogating a transmission line under pressure with a negative pressure impulse, whereby the frequency domain transfer function response is sensed by a transducer and converted into an electrical signal. By adjusting on a real time basis, the center frequency and preferably the notch depth of an active notch filter in accordance with the signal obtained from the impulse response of the pressure line, it is possible to obtain a flat frequency response over a given band width for the active filter and thus compensate for dynamic changes that occur in the pressure measurement system over time, as easily as flushing a line or zeroing the transducer as is done in the prior art.

BRIEF DESCRIPTION OF THE DRAWINGS

The present invention will be better understood in view of the following detailed description thereof when taken with the appended drawings, wherein.

DETAILED DESCRIPTION OF THE INVENTION

Figure 1:
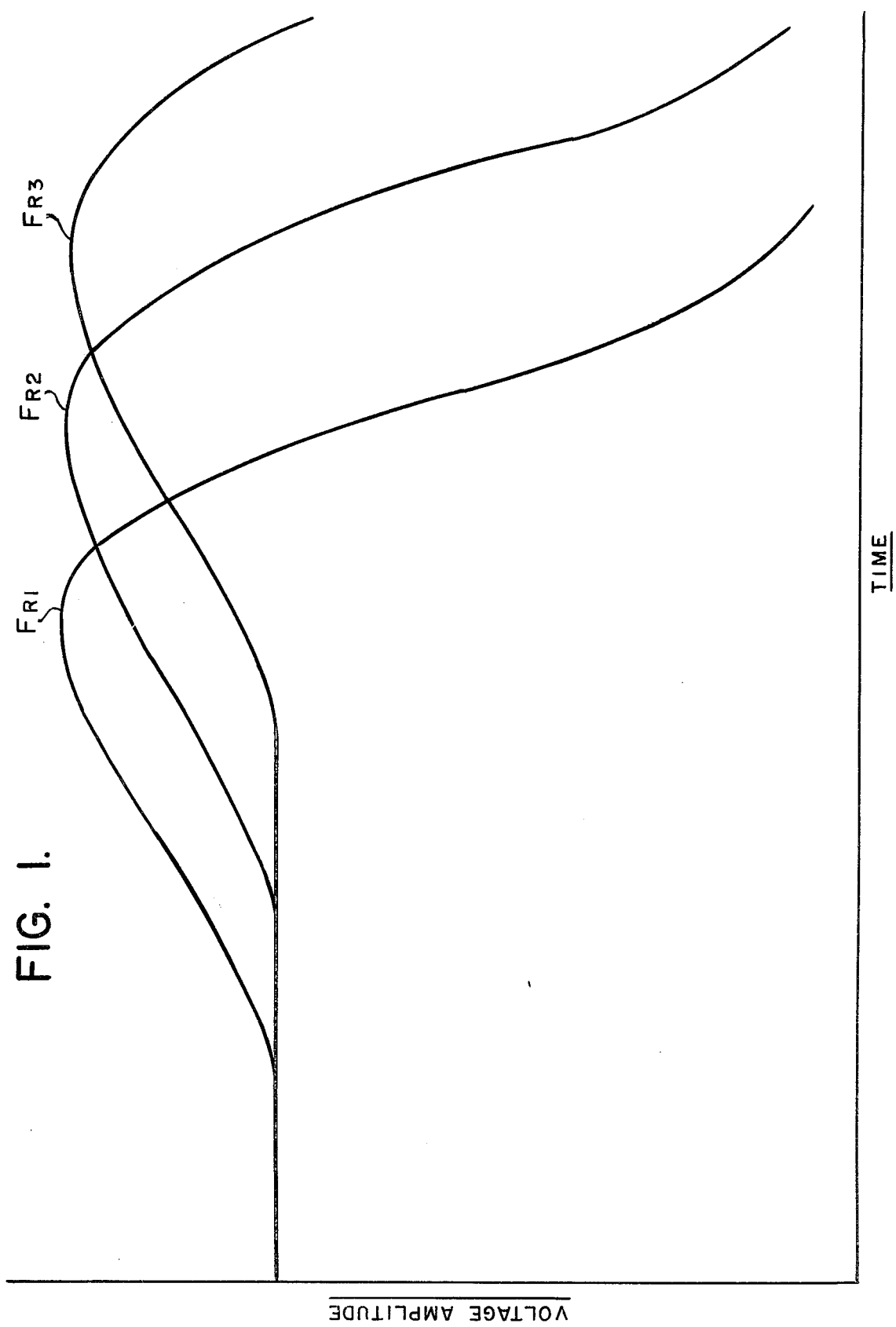
FIG. 1 is a waveform diagram of the frequency characteristic of the pressure system to be measured.

The compensation system carried out by the real time adaptive filtering according to the present invention assumes that the fluid filled pressure transmission line, such as a tubular invasion device, i.e. a catheter, can be described as a slowly time varying second order underdamped low pass system, having a family of responses as shown in FIG. 1 as curves $F_{R1}$, $F_{R2}$ and $F_{R3}$.

Figure 2:
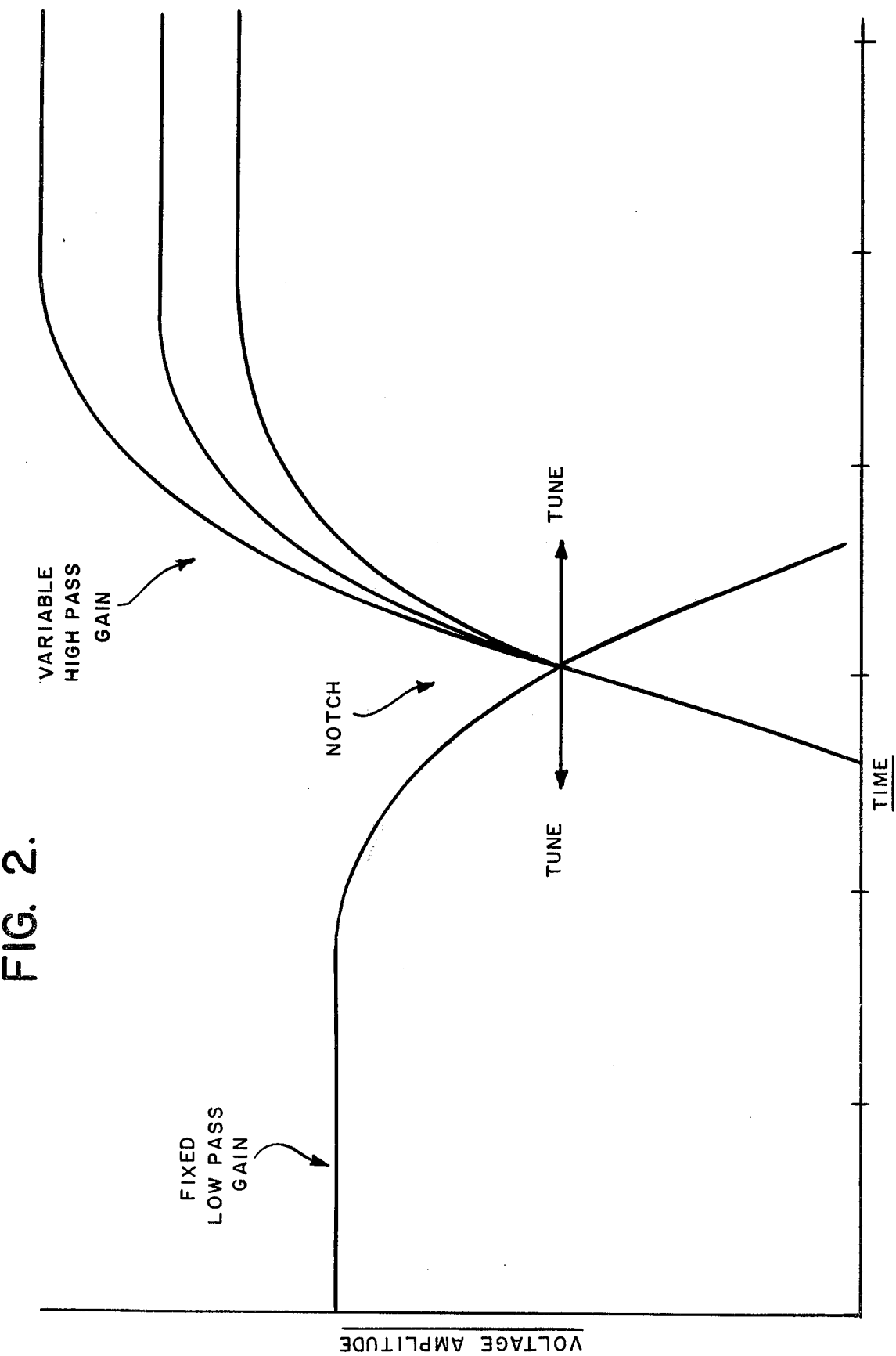
FIG. 2 is a waveform diagram of a notch filter according to the present invention.

The filtering according to the present invention is preferably carried out by an active filter having the characteristics shown in FIG. 2. FIG. 2 illustrates the general characteristics of a tunable notch filter having a fixed low pass gain, which in the present invention is preferably set at 1, and a variable high pass gain of $K > 1$. By varying the center frequency of the notch filter, the resonant frequency of a pulsed transmission line can be obtained by examining the response thereto, since the minimum peak overshoot will be obtained when the center frequency of the notch filter is at the resonant frequency of the transmission line. The notch filter can further be adapted to the characteristics of the transmission line by adjusting the notch depth by again obtaining the minimum peak overshoot, so as to yield an approximately flat response over a wide range of frequencies for the transmission line-filter combination.

Figure 3:
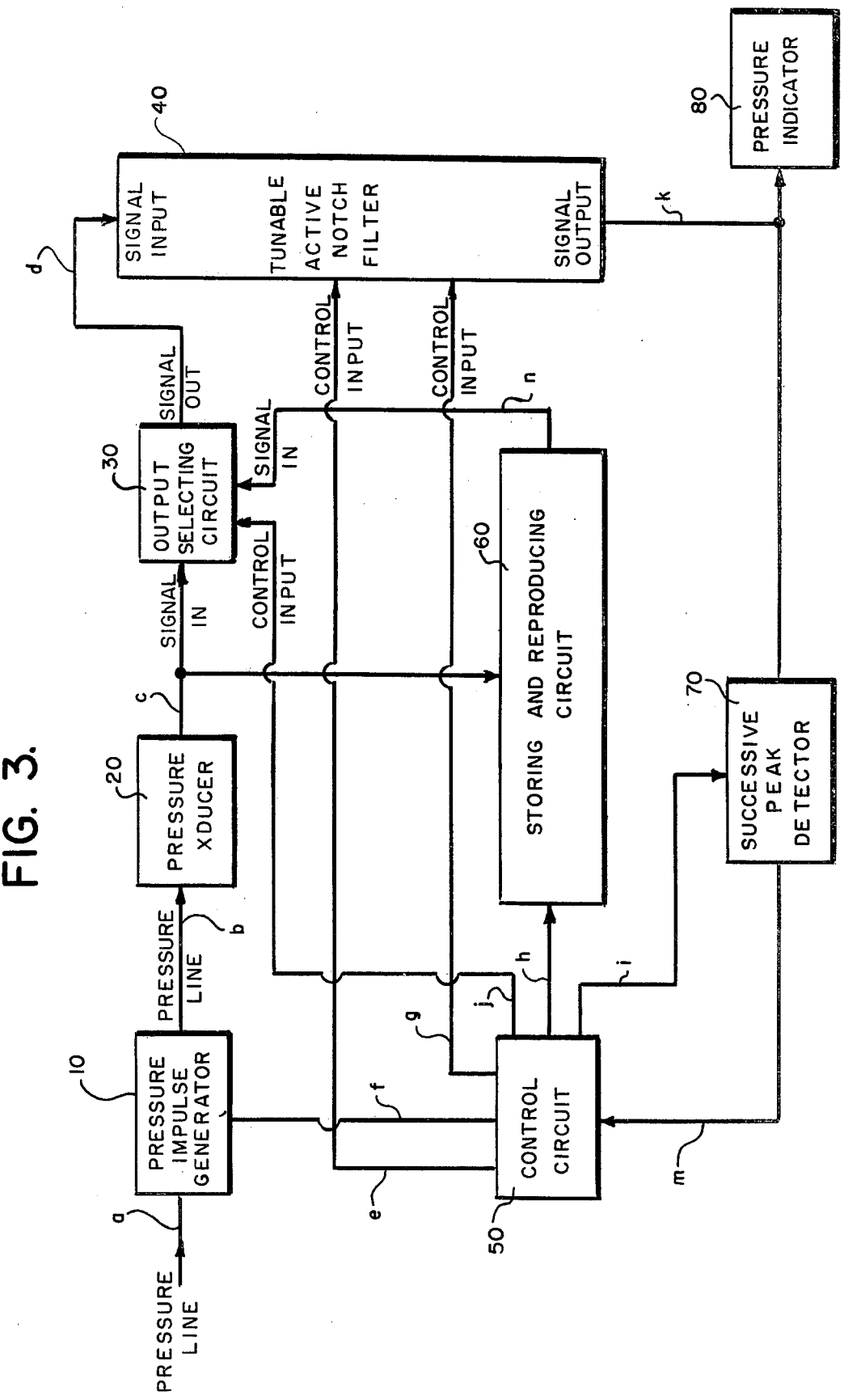
FIG. 3 is a block diagram of the system according to the present invention.

FIG. 3 shows a block diagram of the system utilized for the process of adapting a tunable active notch filter to the frequency domain characteristics of a pressure line a by a time domain processing so as to generate a signal output at line k which has an approximately flat response over a wide range of frequencies of interest so that pressure indication can be carried out in a pressure indicator 80.

In accordance with the present invention, a pressure impulse generator 10 is interposed in the pressure line a and connected by a pressure line b to a pressure transducer 20 which converts pressure values into electrical signals representative thereof. The function of the pressure impulse generator 10 for a patient-catheter application is to apply a single negative pressure impulse or step in the pressure line so as to yield a frequency domain transfer function response in the pressure line a, b which is sensed by the pressure transducer 20 which produces a distorted pressure pulse at output line c. The single pressure impulse applied by pressure impulse generator 10 is effected by control circuit 50 along control line f as will be described hereinafter in greater detail.

The output of pressure transducer 20 is applied along line c to output selecting circuit 30 and normally applied by output selecting circuit 30 along line d to the input of tunable notch filter 40 whose output is fed along line k to the pressure indicator 80. This normal operation is interrupted, during the process of adapting the filter, by control circuit 50 via control line j. Upon the effecting of the pressure impulse by control line f applied to pressure impulse generator 10, the control circuit 50 via control line j, interrupts the feeding of the signal from pressure transducer 20 to the tunable active notch filter and instead, connects the output of storing and reproducing circuit 60 applied via line n to the input of the tunable active notch 40.

During this process, the pressure inpulse signal from pressure transducer 20 is fed to the storing and reproducing circuit 60 which under the control of control circuit 50 via line h, effects storage thereof in a memory device and successively reproduces same at its output so as to be successively applied to the input of the filter 40. During the time that the output of the circuit 60 is successively applied to the filter 40, the signal from the transducer 20 to the notch filter is interrupted by the selecting circuit 30.

The process of adapting the filter to the proper center frequency and notch depth will now be explained. Upon the generation of the impulse to the pressure line, the center frequency of the active filter is set to a maximum, which is beyond any reasonable expected transmission line response, for example 100 Hz in the case of a catheter line. For each successive application of the reproduced pressure inpulse response to the input of the filter 40, the filter frequency is decremented, under the control of control circuit 50 via line e, by a predetermined amount and the output thereof is examined by successive peak detector 70 which under the control of the control circuit 50 via line i, generates a signal at its output along line m when the minimum peak overshoot of the filter is detected.

Upon reaching of the proper center frequency for the notch filter 40, the decrementing of the center frequency is terminated by the control circuit 50 and the center frequency of the filter is maintained. Immediately thereafter, the control circuit 50 controls, via control line g the notch depth from a maximum value which is decremented by a predetermined amount until a minimum peak overshoot is detected by the peak detector 70 whereupon the decrementing of the notch depth is terminated and the value is maintained. It should be noted that while the active filter will yield good results with the turning of only the center frequency thereof and with the notch depth set at some intermediate or average level, the additional tuning of the notch depth enables one to obtain an approximately flat response for the filter over a wide range of frequencies and thus is highly preferable.

Upon the termination of the tuning of both the center frequency and notch depth, the filter 40 is now adapted to the frequency characteristics of the pressure line a and is thus ready to effect normal operation so that pressure can be indicated by pressure indicator 80. At this point, the control circuit 50 via control line j, interrupts the path of the output of the storing and reproducing circuit 60 to the output line d of the selecting circuit 30 and resumes the application of the output of the pressure transducer 20 to the input of the notch filter 40 so that the signals produced by the pressure transducer 20 and representative of the pressure in line a will be indicated at pressure indicator 80.

It should be noted that the adapting of the filter 40 to the frequency domain characteristics of the pressure line a is carried out by a time domain analysis in real time and thus affords a relatively simple and fast compensation of any changes in the pressure line characteristic. The adapting process can be started manually by a push-button, such as described hereinafter, or can be carried out periodically under the control of an automatically actuating timing system, such as a computer.

Figure 4:
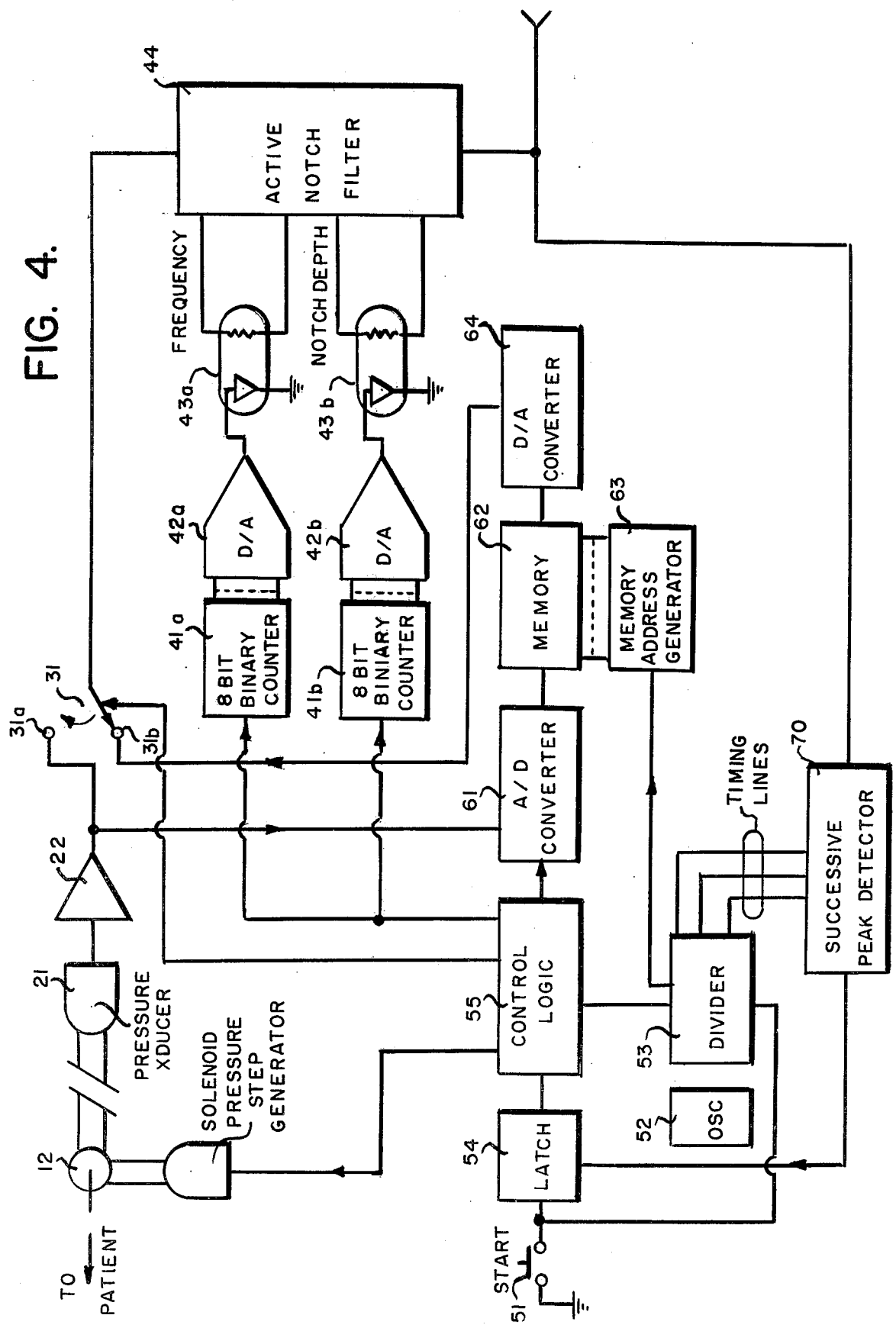
FIG. 4 is a more detailed block diagram of the elements of FIG. 3.

FIG. 4 shows a more detailed block diagram of the structure of the present invention as shown in FIG. 3. As shown in FIG. 4, the pressure impulse generator includes an electrically actuatable pressure solenoid 11 and a valve 12 which enables the negative pressure impulse to be input to the pressure line. These elements 11 and 12 are considered to be conventional fluid control devices and are therefore not discussed in any greater detail.

The pressure transducer 20 consists of a pressure sensing element 21 and an amplifier 22 which amplifies the output thereof to levels which are usable for processing through the notch filter 40. Both the pressure sensor 21 and the amplifier 22 are also well known conventional devices and need not be further described.

The output selecting circuit 30 is shown in a representational form as a simple two pole analog switch 31 which is switchable in response to a control signal from the control circuit 50. The storing and reproducing circuit 60 includes an A-D converter 61 which receives at its input the output of the amplifier 22. The A-D converter 61 takes the output of the pulse response from the pressure line, which has been converted to a signal at the output of amplifier 22, and converts it into a digital form which can be written into memory circuit 62 under the control of a memory address register 63 which is in turn controlled by the control circuit which feeds a clock signal thereto obtained from an oscillator 52 which is divided down and combined in a divider 53 for generating the system timing pulses. The output of the memory circuit 62 is thereafter fed to a D-A converter 64 whose output is received at the input 31b of the switch 31. Under the control of the control circuit via a timing signal, after the step response signal has been converted to digital data and stored in the memory 62, the memory address register continuously accesses the stored digital data and the D-A converter 64 converts it to an analog signal which is successively applied to the input of the notch filter 44. The switch 31 is shown in the state where the notch filter 44 is being adapted to the frequency characteristics of the pressure line and the normal output from amplifier 22 is interrupted.

The control circuit 50 comprises a start switch 51 which in the portrayed embodiments is a single pulsing switch which can be manually operated to start the compensation process. A latch 54 records the pulse from the start switch 51 and applies a signal to the control logic 55 which initiates the pressure step in the line and the switching over of the switch 31 from terminal 31a and 31b to the state shown in FIG. 4. The control logic also thereafter controls the operation of the tunable filter 40.

The tunable filter 40 is shown in FIG. 4 as comprising an active notch filter 44 which is capable of being tuned in its center frequency and its notch depth. This tuning is carried out in two channels by 8 bit binary counters 41a, 41b which feed D-A converters 42a, 42b respectively and which in turn apply analog signals to optoelectric couplers 43a, 43b respectively, which are capable of converting analog signals into corresponding resistance values and which act to respectively adjust the center frequency and notch depth of the filter 44.

The control logic 55 with the timing signals from divider 53, acts to first clock the 8 bit counter 41a and then the 8 bit counter 41b in a down counting mode so as to decrement the output of the D-A converters 42a, 42b and thereby decrease the resistance value output of the optoelectric couplers 43a, 43b. After the filter has been adapted, the switch 31 is actuated to connect the pole 31a and normal filtering is resumed.

Figure 5:
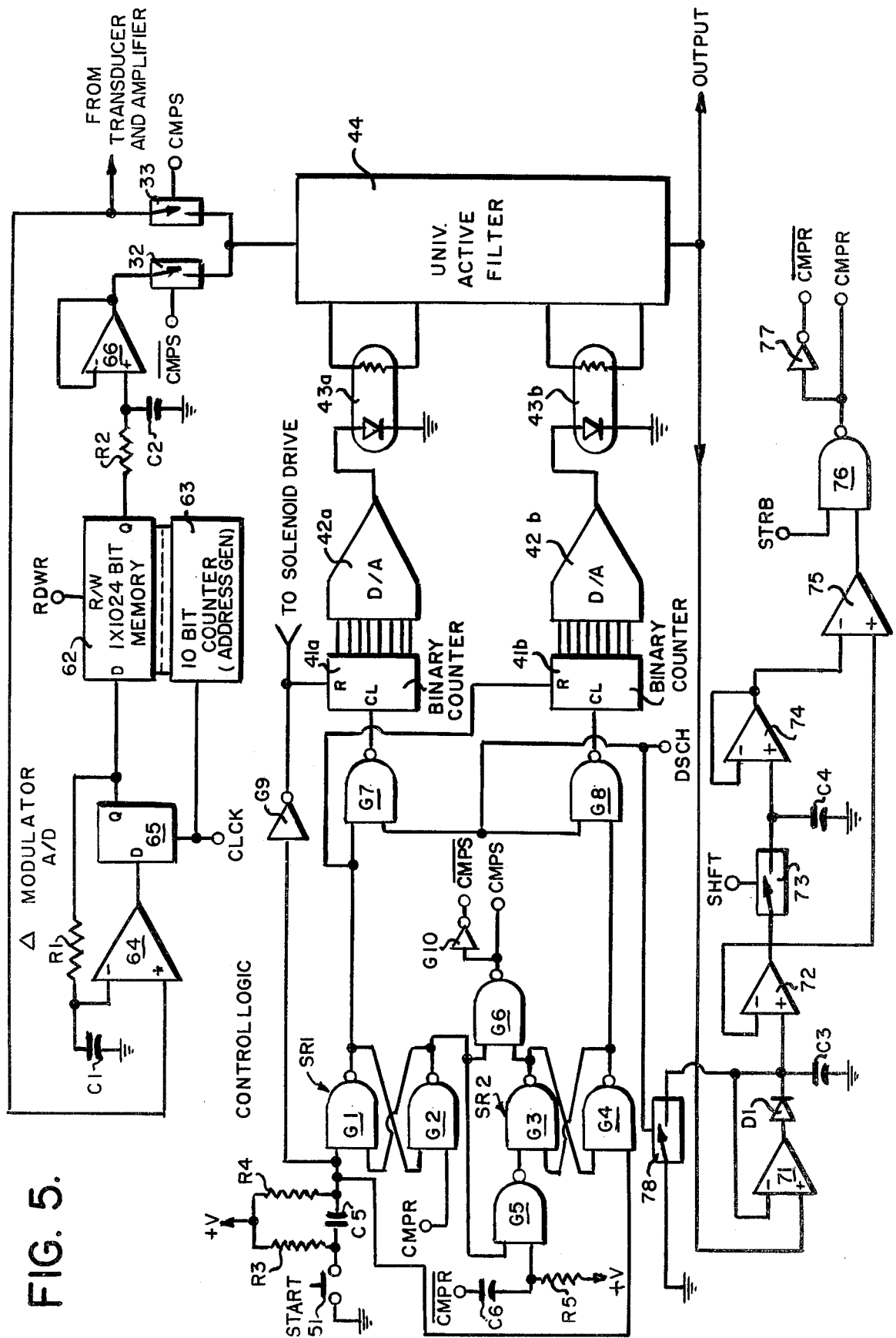
FIG. 5 is a still more detailed schematic of a preferred embodiment according to the invention.
Figure 6:
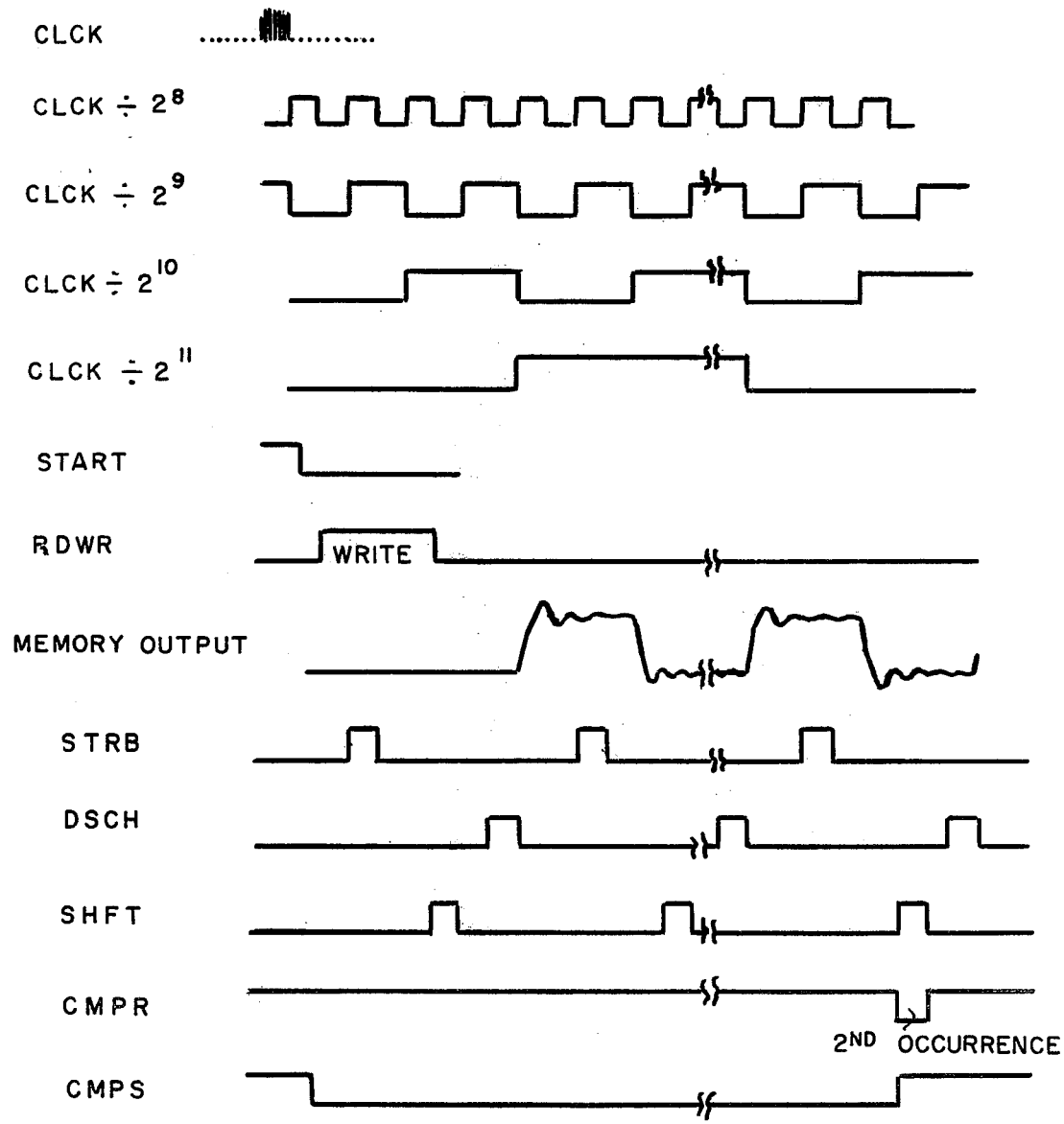
FIG. 6 is a timing diagram of the signals shown in FIG. 5.

FIGS. 5 and 6 are used to illustrate the preferred embodiment of the present invention of elements 30, 40, 50, 60 and 70.

As shown therein, the tunable active notch filter 40 includes 8 bit binary counters 41a, 41b which are of the commonly known 4040 integrated circuit type. The D-A converters 42a, 42b are preferably Analog Devices AD 7523 which are capable of handling 8 bits of input data. The optoelectric couplers 43a, 43b are preferably General Electric H11F3 devices which produce the desired resistance range for controlling the active filter. In particular, the active filter 44 is preferably, what is conventionally accepted as being called a universal active filter, and is preferably the Burr-Brown UAF-31 active filter.

The storing and reproducing circuit 60 is most advantageously carried out by a delta-modulator A/D converter circuit, because of the fact that it inherently provides for both A-D and D-A conversion as will be described. The delta-modulator A-D converter includes amplifier 64 which has the positive input thereof attached to the output of amplifier 22 and the output thereof attached to the D input of a D-type flip-flop 65. The Q-output of flip-flop 65 is fed back into the negative input of the amplifier 64 through an RC circuit comprising resistor R1 and capacitor C1. The flip-flop 65 is clocked by clock signal CLCK which originates from the divider 53 and the relative timing of signal CLCK is shown in FIG. 6. The Q-output of flip-flop 65 is also fed to the data input of a 1×1024 bit memory 62. The memory 62 is controlled by signal RDWR shown in FIG. 6 which enables it to write in the data during the A-D conversion of the pulse input and to thereafter read the data out for reproducing same.

The memory is addressed in all 1024 bits by the 10 bit address register counter 63 which is also clocked by signal CLCK. The output of the memory 62 is fed into a D-A converter including an amplifier circuit 66 which has an RC circuit at the positive input thereof including resistor R2 and capacitor C2 which are preferably equal in value to R1 and C1 respectively so as to obtain the exact output as that input from the amplifier 22. While the delta modulator A-D converter circuit is conventional, it is particularly applicable to the operation of the present invention and thus it is advantageously used herein to reduce the complexity of the circuitry and to effect a relatively fast storing and reproduction of the step response signal.

The output selecting circuit 30 is shown to preferably comprise two analog switches 32, 33 which are preferably conventional 4016 CMOS circuits which are controlled by the signals $\overline{CMPS}$ and CMPS respectively which are generated by the control circuit 50 as will be explained. In normal operation, switch 33 is closed and switch 32 is open so that the output from the amplifier 22 is fed directly into the filter 44 so as to be filtered and passed on to a pressure indicator 80. During the adaption of the filter to the frequency response of the pressure line, switch 33 is open and switch 32 is closed whereby the output of amplifier 66 is connected to the active filter 44.

The successive peak detector 70 is shown in FIG. 5 in its preferred embodiment. As shown, amplifier 71 has the positive input thereof connected to the output of the active filter 44 with the output thereof fed back to the negative input through a diode D1. The output of the diode is applied across a capacitor C3 and is also connected to the positive input of amplifier 72 and the output of the analog switch 78, whose input is connected to ground and whose control input is connected to the timing signal DSCH. Switch 78 is used to effect the discharge of capacitor C3, as will be explained hereinafter.

The output of amplifier 72 is fed back to the negative input thereof and also applied to the positive input of comparator amplifier 75. Further, the output of amplifier 72 is applied to the input of an analog switch 73 whose output is applied across capacitor C4 connected to ground and to the positive input of amplifier 74. The control input of analog switch 73 is controlled by timing signal SHFT which is shown in FIG. 6 and switch 73 is used to shift the voltage across C3 ($V_{C3}$) to C4 and is described in more detail hereinafter. The output of amplifier 74 is fed back to the negative input thereof and is also applied to the negative input of comparator amplifier 75. The output of amplifier 75 is applied to one input of NAND-gate 76 whose other input is connected to timing signal STRB which is shown in FIG. 6 and will be described hereinafter. The output of NAND-gate 76 generates a zero-going pulse CMPR when $V_{C4} > V_{C3}$ and STRB are present. Inverter 77 generates the $\overline{CMPR}$ signal which in combination with CMPR is used by the control logic as will be explained hereinafter.

The peak detector 70 is used both for the tuning of the center frequency and the timing of the notch depth and thus for purposes of explaining the operation thereof, it will only be explained with respect to the tuning of the center frequency.

Upon the depression of switch 51, the binary counter 41a is reset at input R to its maximum value such that the D-A 42a provides a maximum voltage value to the coupler 43a such that the active filter is tuned to this maximum frequency, for example 100 Hz. The step signal which has been stored is now reproduced periodically at the input of the active filter 44. The peak overshoot response for each each successive adjustment of the center frequency is fed to the input of amplifier 71. This value is stored in capacitor C3 so that it can be compared to the last received peak overshoot value stored in C4. The initial peak overshoot value is shifted to capacitor C4 via analog switch 73, which is effected by the control signal SHFT. Immediately thereafter the capacitor C3 is discharged via analog switch 78 as controlled by timing signal DSCH. Timing signal DSCH is also applied to one input of NAND-gate G-7 which acts to clock counter 41a so as to decrement it and thus later the center frequency of the active filter by a predetermined amount. Thus the next application of the reproduced pulse signal to the active filter 44 results in another peak overshoot voltage which is fed to the input of amplifier 71 and stored in capacitor C3. The output voltage $V_{C3}$ of capacitor C3 is applied by the output of amplifier 72 to comparator 75 is compared to the voltage $C_{C4}$ stored in capacitor C4 through amplifier 74. If $V_{C4}$ is less than $V_{C3}$, $V_{C3}$ is transferred to C4 by the shift signal SHFT and capacitor C3 is discharged by signal DSCH a has already been explained and the center frequency of the filter 44 is again decremented. When $V_{C4}$ is greater than $V_{C3}$, the decrementing process stops, since this condition occurs within a negligible error, at the resonant frequency of the transmission line.

This process is again repeated for the parameter of notch depth utilizing the same successive peak detector.

When there is a favorable comparison of $V_{C4}$ greater than $V_{C3}$, the outputs CMPR, $\overline{\text{CMPR}}$ are obtained in synchronism with the STRB pulse which is shown in FIG. 6.

The control circuit 50 including the start switch 51, the latch circuitry 54 and the control logic 55 is shown in detail in FIG. 5. The start switch 51 has one input connected to ground and the other input connected via resistors R3 and R4 across capacitor C5 to the voltage supply +V, to one input of NAND-gate G1 which is interconnected with NAND-gate G2 to form set-reset flip-flop SR1 and to the input of inverter G9 which has the output thereof fed to the input of the solenoid pressure step generator 11 to actuate same during the duration of the pulse to the reset input of counter 41a. The output of G9 can also be used to reset the divider 53, counter 63 and in general to initialize the system. The pulse from switch 51 is also connected to one input of NAND-gate G4 which is interconnected with NAND-gate G3 to form set-reset flip-flop SR2. Thus when switch 51 is depressed, a single zero-going pulse issues therefrom and is fed as a positive going pulse to the solenoid drive to initiate the negative pressure step in the pressure line, to the binary counter 41a to reset it to its maximum value and to initialize the system. Moreover, set-reset flip-flop SR1 is switched so that the output of G1 is at logic 1 and the output of G2 is at logic 0. Set-reset flip-flop SR2 is also set so that G4 has the output thereof at logic 1 and G3 has the output thereof at logic 0. The switching of the output of G1 to logic 1 also effects the continuous reset of counter 41b for the duration of that state of SR1. Moreover, due to thwe fact that both of the outputs of G2 and G3 are at zero, the output of NAND-gate G6 which generates the CMPS signal is at logic 0 and the output of inverter G10 which generates the $\overline{\text{CMPS}}$ signal is at logic 1 so that the selecting circuit 30 is switched over such that analog switch 32 is closed and analog switch 33 is open so that the input of the filter 44 receives the output of amplifier 66.

Since the outputs of gates G1 and G4 are at logic 1, NAND-gate G7 and G8 are enabled to pass clock signal DSCH therethrough to the clock inputs of binary counters 41a, 41b. However, since counter 41b is in a continuous state of reset, the clocking thereof has no effect. This allows only the counter 41a to be decremented during the compensation for the center frequency.

When the peak detector 70 senses that the center frequency has been found, a negative going CMPR pulse and a positive going $\overline{\text{CMPR}}$ pulse is obtained at STRB, which is received respectively at the input of G2 and the input of NAND-gate G5 through an RC circuit including capacitor C6 and resistor R5 connected to +V. G5 has the output thereof connected to one input of G3. Since the output of G2 is at logic 0 when the CMPR pulse is obtained, it acts to set SR1 into the state where the output of G2 is at logic 1 and the output of G1 is at logic 0 so that gate G7 is disenabled to clock counter 41a. Because of the logic 0 state of the output of G2 at the time that the $\overline{\text{CMPR}}$ pulse is received, it has no effect on the output of G5 and thus SR2 remains in its state. Moreover, even though the output of G2 is now at logic 1 the fact that the output of G3 is at logic 0 still maintains the CMPS signal at a logic zero at the output of G6.

The output of G1 is now at a logic 0, and therefore the binary counter 41b is no longer continuously reset and is now enabled to be clocked through gate G8 and it is therefore decremented as described therebefore. Upon the indication of the favorable comparison for the notch depth, the CMPR and $\overline{\text{CMPR}}$ signals are again produced. CMPR has no effect on SR1, but because the output of G2 is at a logic 1 and the $\overline{\text{CMPR}}$ signal goes to a logic 1, the output of G5 becomes a logic 0 and resets SR2 so that G3 is in a logic 1 state and G4 has its output at logic 0. As a result, G8 is disenabled to allow any further clocking of binary counter 41b. Further, the change in the output of G3 is logic 1, changes the output of G6 to a logic 1 and the output of G10 to a logic 0, so that the states of switches 32 and 33 are reversed allowing the output from the amplifier 22 to be normally fed to the filter 44 and through its output to the pressure indicator 80.

One skilled in the art will realize that the initial start-up logic state of the structure shown in FIG. 5 can be reset on the depression of the start button 51, for example, the divider 53 and that the capacitor C3 can be discharged by the initialization including the connection thereof to ground through switch 78. The 10 bit address generator counter 63 can also be reset to zero upon the initialization of the circuitry when the start button is depressed. Moreover the pushbutton 51 can be released by a timing circuit which produces a single pulse periodically to adapt the filter to present conditions, for example every hour, every 12 hours or every 14 hours as experience will dictate.

It should also be understood that the pressure indicator 80 can be a digital or analog meter, may comprise indicator lights or may be a continuous readout such as a CRT device, for example an oscillascope.

It will be appreciated that the instant specification and claims are set forth by way of illustration and not limitation, and that various modifications and changes may be made without departing from the spirit and scope of the present invention.

What is claimed is:

1. In a process for measuring the catheter fluid pressure of a patient using a pressure transmission line and a pressure transducer to convert the pressure into an electrical signal and indicating the patient pressure corresponding to the electrical signal with a pressure indicator, the improvement comprising the steps of disposing a tunable active filter in the single path between the transducer and the pressure indicator and adapting the frequency parameters of the filter in real time to that of the catheter by periodically applying a negative pressure impulse to the pressure transmission line instead of the patient pressure to obtain a frequency domain transfer function response to each impulse and adjusting the filter parameters to each impulse response to compensate for inaccuracies in the overall frequency response.

2. The process according to claim 1, wherein the step of adapting for each impulse comprises:
   a. interrupting the application of the output of the transducer to the filter;
   b. applying the negative pressure impulse to the catheter to obtain the frequency domain transfer function response;

c. temporarily storing the signal obtained from the transducer in response to the impulse;
d. periodically reproducing the stored signal and applying each reproduced signal to the input of the filter;
e. incrementally adjusting the center frequency of the filter for each application of the reproduced signal until the resonant frequency of the catheter is determined whereby the filter is adapted to the resonant frequency of the catheter; and
f. reapplying the output of the transducer to the input of the adapted filter.

3. The process according to claim 2, wherein the step of adapting further comprises, prior to reapplying the output of the transducer to the input of the adapted filter, the step of incrementally adjusting the notch depth of the filter until a substantially flat bandwidth response is obtained.

4. The process according to claim 2, wherein the step of incrementally adjusting the center frequency comprises setting the center frequency to a maximum frequency value, decrementing the center frequency in predetermined steps until the resonant frequency is determined by comparing the peak overshoot response of the filter to that for the previous center frequency and stopping the decrementing when the minimum peak overshoot value is determined.

5. The process according to claim 3, wherein the step of incrementally adjusting the center frequency comprises setting the center frequency to a maximum frequency value, decrementing the center frequency in predetermined steps until the resonant frequency is determined by comparing the peak overshoot response of the filter to that for the previous center frequency and stopping the decrementing when the minimum peak overshoot value is determined and wherein the step of incrementally adjusting the notch depth comprises setting the notch depth to a maximum value, decrementing the notch depth in predetermined steps until a substantially flat bandwidth is obtained by comparing the peak overshoot response of the filter to that of the previous notch filter depth and stopping the decrementing when the minimum peak overshoot is determined.

6. The process according to claim 3, wherein the step of temporarily storing comprises converting the signal to a digital form by delta modulation.

7. In an apparatus for measuring the catheter fluid pressure of a patient of the type having a pressure transmission line, a pressure transducer for converting catheter pressure into an electrical signal and a pressure indicator for indicating patient corresponding to the electrical signal, the improvement comprising a tunable active notch filter disposed in the signal path between the transducer and the indicator and means for adapting the frequency parameter of the filter in real time to the frequency characteristics of the catheter comprising means for periodically applying a negative pressure impulse to the pressure transmission line instead of the patient pressure to effect a frequency domain transfer function response to each impulse and means for adjusting the parameters of the filter to each impulse response to compensate for inaccuracies in the overall frequency response.

8. The apparatus according to claim 7, wherein the means for adapting further comprises
a. means for temporarily storing the signal obtained from the transducer in response to each impulse;
b. means for periodically reproducing the stored signal;
c. means responsive to the application of each pressure impulse for interrupting the application of the output of the transducer to the filter and for connecting the output of the reproducing means to the input of the filter to apply each reproduced signal to the filter and responsive to an indication that the filter has been adapted for reapplying the output of the transducer to the input of the adapted filter; and
d. means for incrementally adjusting the center frequency of the filter for each application of the reproduced signal until the resonant frequency of the catheter is determined, whereby the filter is adapted to the resonant frequency to the catheter.

9. The apparatus according to claim 8, wherein the means for adapting further comprises means for incrementally adjusting the notch depth of the filter, until a substantially flat bandwidth is obtained and for indicating that the filter is adapted at the termination of the adjustment.

10. The apparatus according to claim 8, wherein the means for incrementally adjusting the center frequency comprises means for setting the center frequency to a maximum frequency value, means for decrementing the center frequency in predetermined steps until the resonant frequency is determined including means for comparing the overshoot response of the filter to that for the previous center frequency and means for stopping the decrementing when the minimum peak overshoot value is determined.

11. The apparatus according to claim 9, wherein the means for incrementally adjusting the center frequency comprises means for setting the center frequency to a maximum frequency value, means for decrementing the center frequency in predetermined steps until the resonant frequency is determined including means for comparing the overshoot response of the filter to that for the previous center frequency and means for stopping the decrementing when the minimum peak overshoot value is determined and wherein the means for incrementally adjusting the notch depth comprises means for setting the notch depth to a maximum value, means for decrementing the notch depth in predetermined steps until substantially flat bandwidth is obtained comprising means for comparing the peak overshoot response of the filter to that for the previous notch depth and means for stopping the decrementing when the minimum peak overshoot is determined.

12. The apparatus according to claim 9, wherein the means for temporarily storing comprises means for converting the signal to digital form comprising a delta modulator.

13. A device for effecting the real time adaptive filtering of the electrical signal output of a pressure transducer sensing fluid pressure in a pressure line, comprising:
a. a tunable active notch filter for receiving the output of the transducer at the input thereof;
b. means for periodically applying a negative pressure impulse to the pressure line instead of the fluid pressure to obtain a frequency domain transfer function response to each impulse; and
c. means for adjusting the tunable parameters of the active filter to each impulse response to compensate for the frequency response of the pressure line.

14. The device according to claim 13, wherein the means for adjusting comprising means temporarily storing the signal obtained from the transducer in response to each impulse; means for successively reproducing the stored signal; means responsive to the application of each pressure impulse for interrupting the application of the output of the transducer to the filter and for connecting the output of the reproducing means to the input of the filter to apply each reproduced signal to the filter and responsive to an indication that the filter has been adapted for reapplying the output of the transducer to the input of the adapted filter, and means for incrementally adjusting the center frequency of the filter for each application of the reproduced signal until the resonant frequency of the pressure line is determined, whereby the filter is adapted to the frequency characterisation of the pressure line.

15. The device according to claim 14, further comprising means for incrementally adjusting the notch depth of the filter until a substantially flat bandwidth is obtained and for indicating that the filter is adapted at the termination of the adjustment.

16. The device according to claim 15, wherein the means for incrementally adjusting the center frequency comprises means for setting the center frequency to a maximum frequency value, means for decrementing the center frequency in predetermined steps until the resonant frequency is determined including means for comparing the overshoot response of the filter to that for the previous center frequency and means for stopping the decrementing when the minimum peak overshoot value is determined and wherein the means for incrementally adjusting the notch depth comprises means for setting the notch depth to a maximum value, means for decrementing the notch depth in predetermined steps until a substantially flat bandwidth is obtained comprising means for comparing the peak overshoot response of the filter to that for the previous notch depth and means for stopping the decrementing when the minimum peak overshoot is determined.

17. The device according to claim 14, wherein the means for incrementally adjusting the center frequency comprises means for setting the center frequency to a maximum frequency value, means for decrementing the center frequency in predetermined steps until the resonant frequency is determined including means for comparing the overshoot response of the filter to that for the previous center frequency and means for stopping the decrementing when the minimum peak overshoot value is determined.

18. The device according to claim 14, wherein the means for temporarily storing comprises means for converting the signal to digital form comprising a delta modulator.

* * * * *

UNITED STATES PATENT AND TRADEMARK OFFICE
CERTIFICATE OF CORRECTION

PATENT NO. : 4,325,382
DATED     : April 20, 1982
INVENTOR(S) : Saul Miodownik

It is certified that error appears in the above-identified patent and that said Letters Patent is hereby corrected as shown below:

Column 6, line 57:   change "later" to -- alter --.

Column 7, line 38:   change "thwe" to -- the --.

Column 10, line 66:  change "comprising" to -- comprises --.

Signed and Sealed this

Seventh Day of June 1983

[SEAL]

Attest:

DONALD J. QUIGG

Attesting Officer    Acting Commissioner of Patents and Trademarks